United States Patent [19]

Hawkins

[11] Patent Number: 4,971,490
[45] Date of Patent: Nov. 20, 1990

[54] FLEXIBLE GUIDE WIRE WITH IMPROVED MOUNTING ARRANGEMENT FOR COIL SPRING TIP

[75] Inventor: Jeffrey S. Hawkins, Micanopy, Fla.

[73] Assignee: National Standard Company, Niles, Mich.

[21] Appl. No.: 409,116

[22] Filed: Sep. 19, 1989

Related U.S. Application Data

[63] Continuation of Ser. No. 162,756, Mar. 1, 1988, abandoned.

[51] Int. Cl.⁵ ............................................. A61B 5/00
[52] U.S. Cl. ................................. 128/772; 128/657; 604/164
[58] Field of Search .................. 128/200.26, 657, 772; 604/164, 170, 280, 281, 282

[56] References Cited

U.S. PATENT DOCUMENTS

| | | | |
|---|---|---|---|
| 3,789,841 | 2/1974 | Antoshkiw | 128/772 |
| 3,906,938 | 9/1975 | Fleishacker | 128/772 |
| 4,538,622 | 9/1985 | Samson et al. | 128/657 |
| 4,548,206 | 10/1985 | Osborne | 128/772 |
| 4,721,117 | 1/1988 | Mar et al. | 128/772 |

Primary Examiner—J. L. Kruter
Assistant Examiner—Randy Shay
Attorney, Agent, or Firm—Emrich & Dithmar

[57] ABSTRACT

A flexible guide wire for use in the placement of a surgical instrument or the like within a human or animal body includes an elongated shaft with a coil spring mounted on its distal end, the shaft being tapered at its distal end to enhance its flexibility, and the shaft having a stepped down portion near its distal end defining a reduced diameter portion for the shaft which is less than the inner diameter of the coil spring to facilitate attachment of the coil spring thereto while providing a smooth transition between the shaft and the coil spring at their junction point.

19 Claims, 1 Drawing Sheet

FIG. 1
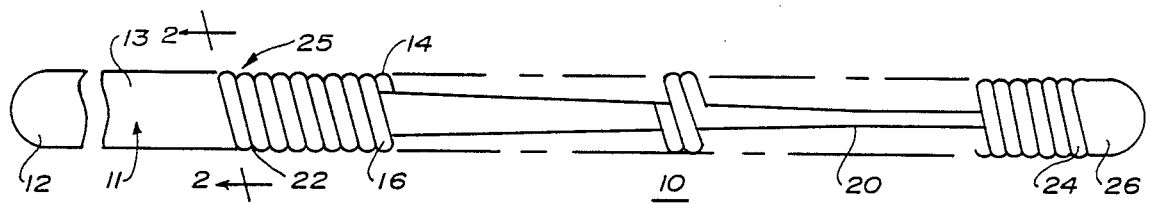
FIG. 2    FIG. 2A
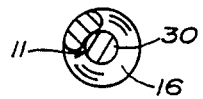 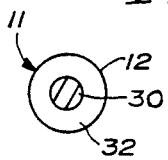
FIG. 3
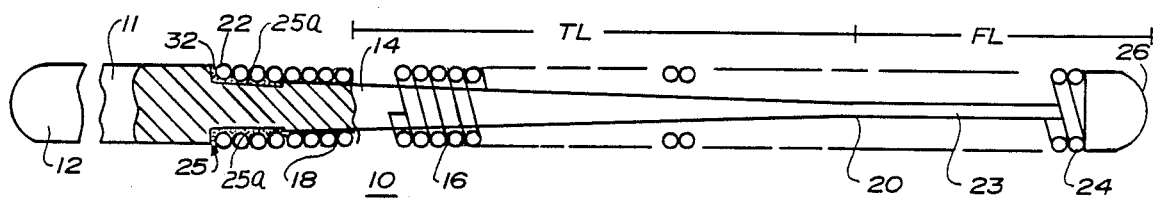
FIG. 4
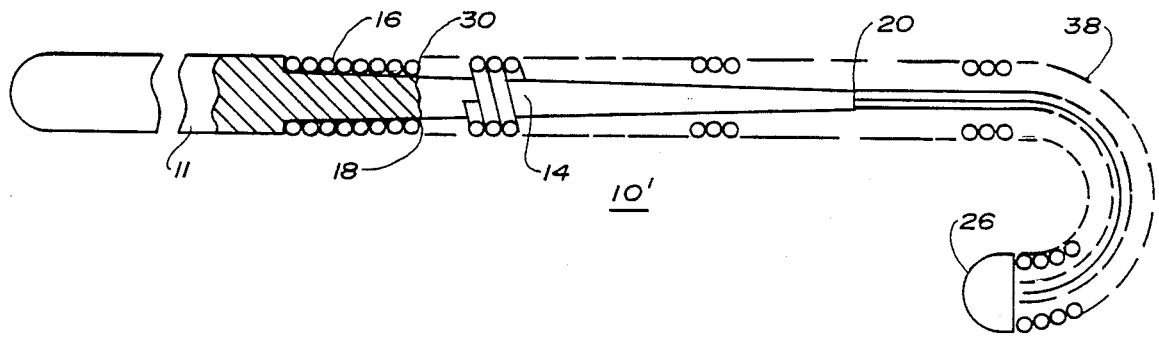
FIG. 5
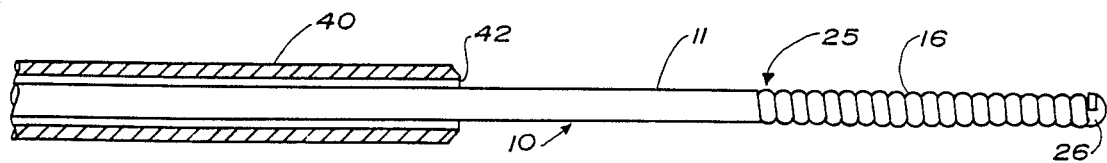

FLEXIBLE GUIDE WIRE WITH IMPROVED MOUNTING ARRANGEMENT FOR COIL SPRING TIP

This application is a continuation of application Ser. No. 162,756, filed Mar. 1, 1988, which is now abandoned.

BACKGROUND OF THE INVENTION

This invention relates to torqueable guide wires for use in guiding the placement of surgical instruments within a human or animal body during micro-invasive procedures.

The use of small needle systems in micro-invasive procedures in various medical fields has become routine because small gauge needles can pass through most of the anatomy without causing significant damage to the anatomy. Such needle systems are used extensively in cardiovascular procedures, and in the fields of radiology and urology, as well as in other medical fields.

Such needle systems generally include a relatively small guide needle which is used to guide a larger hollow catheter to the target within a human body or a veterinary body. The guide needle is directed to the proximity of the target using a hollow cannula. The cannula is inserted into the body and positioned, using fluorscopic techniques, for example, with its distal end contacting or adjacent to an organ or other mass within the body. The guide wire is then advanced through the cannula to the organ or mass and into the organ or mass to the target area. The cannula is then removed and the catheter is advanced over the guide wire and into the organ or mass to the target area.

Guide wires presently in use comprise, a composite structure including a relatively rigid wire or rod with a coil spring attached by welding or soldering to its distal end, defining a flexible or "floppy" tip for the guide wire. The "floppy" tip enables the guide wire to be directed through curving vessels and around obstacles as the tip of the guide wire is being advanced into an organ or other structure of the body without causing damage to the organ or body structure. To further enhance the flexibility of the distal end of the guide wire, the solid wire or rod may be tapered at its distal end with the coil spring extending over the tapered distal portion of the wire or rod and secured to the wire or rod at the point at which the taper begins.

In use, the guide wire is advanced to the desired location within the body through a cannula. The cannula is then removed and a catheter is advanced over the guide wire to the target within the body.

One significant shortcoming of known guide wires of the type including a coil spring tip, is that current techniques for securing the proximal end of the coil spring to the distal end of the solid wire, result in a discontinuity, such as a bump or gap or uneven surface at the junction of the wire and coil spring tip. This results from the way that the coil spring is positioned on the tapered shaft of the wire. Typically, the coil spring is slid onto the tapered distal end of the shaft and advanced until its proximal end assumes an interference relationship with the surface of the tapered rod. Because of this gap or uneven surface, as the guide wire is advanced through a cannula, the guide wire may "catch" on the cannula at its distal tip because of the discontinuity or uneven surface at the junction of the coil spring and the wire. This could result in the coil spring tip being broken off. Also, when the catheter is advanced over the guide wire, there is a tendency for the catheter to "catch" on this discontinuity or uneven surface, and with continued advancement of the catheter, the guide wire might be moved out of position.

Various attempts have been made to alleviate this problem. For example, in one arrangement, a teflon coating is provided over the entire extent of the guide wire. However, this arrangement does not eliminate the bump or extension at the junction point, but merely provides a smoother glide surface for the inner surface of the cannula.

SUMMARY OF THE INVENTION

It is an object of the invention to provide an improved torqueable guide wire.

Another object of the invention is to provide a guide wire for use in placement of surgical instruments and which is substantially immune to damage in use.

Yet another object of the invention is to provide an improved guide wire of the type including a solid wire portion and a coil spring encircling the distal end of the wire providing a flexible portion thereat which is characterized by a smooth transition between the wire and the coil spring.

A further object of the invention is to provide an improved guide wire of the type including a solid wire having a tapered distal end portion and a helical coil spring positioned around the tapered end portion of the wire, wherein the outer diameter of the coil spring corresponds to the outer diameter of the wire at its largest cross section, providing a guide wire characterized by a smooth transition between the coil spring and the main body portion of the needle.

These and other objects are achieved by the present invention which has provided a flexible guide wire which comprises an elongated cylindrical shaft having a main body portion of a given outer diameter, a proximal end and a distal end, said shaft having a stepped down portion near its distal end defining a reduced diameter shaft portion with a generally annular planar end surface for said shaft facing said distal end of said shaft and extending outward radially from said reduced diameter shaft portion, a coil spring having a proximal end and a distal end, said coil spring enclosing said distal end of said shaft with the proximal end of said coil spring encircling said reduced diameter portion of said shaft end and abutting said planar end surface of said shaft, and means securing said proximal end of said coil spring to said shaft near its reduced diameter portion, the outer diameter of said coil spring being substantially the same as said given diameter, providing a smooth transition for the outer surface of the guide wire at the junction of said shaft and said coil spring.

The invention consists of certain novel features and structural details hereinafter fully described, illustrated in the accompanying drawings, and particularly pointed in the appended claims, it being understood that various changes in the details may be made without departing from the spirit, or sacrificing any of the advantages of the present invention.

DESCRIPTION OF THE DRAWINGS

For the purpose of facilitating and understanding the invention, there is illustrated in the accompanying drawings a preferred embodiment thereof, from an inspection of which, when considered in connection with the following description, the invention, its construction and operation, and many of its advantages will be readily understood and appreciated.

FIG. 1 is a plan view of a guide wire provided by the present invention;

FIG. 2 is a sectional view taken along the lines 2—2 of FIG. 1;

FIG. 2A is a view similar to FIG. 2, but with the coil spring removed;

FIG. 3 is a plan view, partially in section of the guide wire shown in FIG. 1;

FIG. 4 is a view similar to FIG. 3 of a guide wire having an alternative tip end; and FIG. 5 illustrates the guide wire of the present invention positioned within a cannula, catheter or the like.

DESCRIPTION OF PREFERRED EMBODIMENTS

Referring to FIG. 1, there is shown a guide wire 10 provided by the present invention for use in micro-invasive procedures in radiology, cardiovascular procedures, urology or in other medical fields. The guide wire is used for placement of surgical instruments or devices within a human or veterinary body.

Referring to FIGS. 1-3 of the drawings, the guide wire 10 of the present invention includes a solid mandrel or needle 11 having a main body portion 12, a proximal end 13 and a distal end 14 and a helical wound coil spring 16 mounted on the distal end 14 of the mandril 11.

The mandril 11 tapers over a portion of its distal end from a point 18 to a point 20 near its tip. The distance between the two points 18 and 20 defines a taper length TL for the guide wire. The distance from the point 20 to the tip 21 of the mandril 11 defines a flop length FL for the guide wire 10. The tip portion 23 of the wire or mandril may be of circular cross section or may be formed with a rectangular cross section.

The coil spring 16 has a proximal end 22 and a distal end 24. The coil spring 16 extends over the distal end 14 of the mandril 11, overlying its taper length and flop length. The coil spring 16 is connected at its proximal end 22 to the mandril 11 at junction area indicated at 25. The coil spring 16 also is connected by welding or otherwise to the end of the tapered portion to form a distal tip 26 having a rounded outer surface.

In accordance with the invention, the junction area 25, whereat the proximal end 22 of the coil spring 16 is attached to the mandril 11, is stepped down from the outer diameter of the wire to the inner diameter of the coil as shown best in FIG. 2A, defining a shaft portion 30 of a reduced diameter and an annular surface 32 facing the distal end or tip of the guide wire. This enables the proximal end 22 of the coil spring 16 to be butted up against surface 32 defined by the stepped down portion and secured in place with solder 25a. As a result, this provides a very smooth transition between the coil 16 and the mandril 11 which facilitates relative movement between the guide wire and a catheter or cannula, and virtually eliminates the chance of the guide wire catching on the catheter or cannula during use of the guide wire.

By way of example, the wire or mandril 11 may be made of 304 vacuum melted stainless steel. The taper can be formed either by drawing the material, or by grinding a piece of wire to the desired taper. The taper size at the stepped down point is provided by grinding away the wire to achieve the desired size for the stepped down portion. The diameters of the mandril or wire and the length of the mandril or wire will vary on the required size and tip action. Tapers of thirty centimeters or more can be provided with a flop at 0.004 inches, providing an additional fifteen centimeters of length, without welds or soldering.

In one embodiment, the wire or mandril 11 had an outer diameter of 0.018 and had a stepped down portion diameter of 0.011. The diameter of the wire or mandril in the flop length area FL was 0.005. The taper length TL from where the shank begins to taper to its taper point, was 4 inches. The axial length of the stepped down portion of the shank was in the range of 0.25 to 0.75 inches and preferably 0.50 inches. The overall length of the distal end portion from the shoulder to the tip was ten inches.

The coil spring 16 may be made of 304 vacuum melted stainless steel, or platinum alloys or other appropriate alloys. It may be formed from 0.007-0.001 diameter coil wire. The proximal end 22 is secured to the stepped down portion of the mandril 11 by welding or soldering. The tip 26 is secured to the distal end 24 of the coil spring 16 and to the tip of the needle or mandril 11 by welding.

With reference to FIG. 4, in accordance with a further embodiment, guide wire 10' includes a "J-tip" end 38 to provide enhanced flexibility for the guide wire 10'.

With reference to FIGS. 3 and 5, the smooth transition between the coil spring 16 and the mandril 11, facilitates relative movement between the guide wire and a hollow surgical instrument or device, such as a catheter or cannula, indicted by reference numeral 40. For example, if the instrument or device is a cannula, which is used to position the guide wire at a target area within a body, the guide wire 10 can be advanced within the cannula, as shown in FIG. 5, without the transition point between the coil spring 16 and the mandril 11 catching on the interior of the cannula, at the distal tip 42 of the cannula 40. Similarly, if the instrument or device 40 is a catheter, and the guide needle is used to position the catheter at a target within the body, the catheter can be advanced along the guide wire without the distal tip 42 of the catheter catching on the guide wire 10 at the junction point.

The improved construction for a guide wire afforded by the present invention, in which the portion of the mandril immediately proximal of its tapered distal end is stepped down from the outer diameter of the main body portion of the mandril to a size corresponding to the inner diameter of the coil spring. This construction enables the proximal end of the coil spring to be butted up against the mandril. Also because the outer diameter of the coil spring is substantially the same as the outer diameter of the main body portion of the mandril, the guide wire defines a smooth transition at the junction point between the coil spring and the mandril.

I claim:

1. A flexible guide wire comprising:
an elongated cylindrical metal wire having a main body portion of a given outer diameter, a proximal end and a distal end,
said metal wire having a stepped down portion near its distal end defining a reduced, uniform diameter portion with a generally annular planar metallic end surface for said wire facing said distal end of said wire and extending outward radially from said reduced diameter portion,
a coil spring having a proximal end and a distal end, said coil spring enclosing said distal end of said wire with a plurality of convolutions of said coil spring at the proximal end of said coil spring encircling said reduced diameter portion of said wire distal end and the most proximal convolution abutting said planar metallic end surface of said wire, and means securing said proximal end of said coil spring to said wire at the reduced diameter portion thereof, the junction of said main body portion of said wire and the most proximal convolutions of said coil spring being substantially free of plastic material, the outer diameter of said coil spring being substantially the same as said given diameter, providing a smooth transition for the outer surface of the guide wire at the junction of said main body portion of said wire and said proximal end of said coil spring.

2. A guide wire according to claim 1, wherein at least said main body portion of said cylindrical metal wire has a uniform outer diameter.

3. A guide wire according to claim 1, wherein the length of said reduced diameter portion of said metal wire is in the range of about 0.25 to 0.75 inches.

4. A guide wire according to claim 1, wherein said means securing said proximal end of said coil spring to said metal wire comprises solder.

5. A guide wire according to claim 1, wherein said means securing said proximal end of said coil spring to said metal wire comprises a weld.

6. A guide wire according to claim 1, wherein the inner diameter of said coil spring corresponds to the outer diameter of said reduced diameter portion of said metal wire.

7. A guide wire according to claim 1, wherein said distal end of said metal wire extends within said coil spring to said distal end of said coil spring, and said distal end of said metal wire is secured to said distal end of said coil spring.

8. A guide wire according to claim 7, which further comprises a rounded tip secured to the distal end of said metal wire and to the distal end of said coil spring.

9. A guide wire according to claim 1, wherein said distal end of said metal wire includes a tapered portion.

10. A guide wire according to claim 9, wherein said distal end of said metal wire is tapered over only a portion of its axial extent.

11. A guide wire according to claim 9, wherein said tapered portion of said wire has a generally rectangular cross section.

12. A flexible guide wire for use in the placement of a hollow tubular surgical instrument within a human or veterinary body, said guide wire comprising:

an elongated cylindrical metal wire having a main body portion of a given diameter, a proximal end and a distal end, said distal end of said wire having a tapered portion, a coil spring having a proximal end and a distal end, the portion of said wire immediately proximal its tapered distal end being stepped down from the outer diameter of said main body portion of said wire to a size corresponding to the inner diameter of said coil spring, defining a reduced, uniform diameter portion with a generally annular planar metallic end surface for said wire intermediate its main body portion and its tapered portion;

said coil spring enclosing the distal end of said wire with a plurality of convolutions of said coil spring at the proximal end of said coil spring encircling said reduced diameter portion of said wire and the most proximal convolution abutting said planar metallic end surface, and means securing said proximal end portion of said coil spring to said wire at the reduced diameter portion thereof, the junction of said main body portion of said wire and the most proximal convolutions of said coil spring being substantially free of plastic material, the outer diameter of said coil spring being substantially the same as the outer diameter of said main body portion of said wire, providing a smooth transition for the outer surface of the guide wire at the junction said main body portion of said wire and the most proximal convolutions of said coil spring, thereby facilitating relative movement between the guide wire and the surgical instrument while the guide wire is located within the surgical instrument in use within the body.

13. A torqueable guide wire for use in the placement of a hollow tubular surgical instrument within a human or veterinary body, said guide wire comprising:

an elongated wire of a relatively rigid metal having a main body portion, a proximal end and a distal end, said main body portion having a substantially uniform outer diameter, a relatively flexible, helical wound coil spring having a proximal end and a distal end, said distal end of said wire extending into said coil spring to the distal end of said coil spring, a portion of said wire distal end being tapered to provide a gradual transition in the flexibility of said wire, the portion of said wire immediately proximal its tapered distal end being stepped down from the outer diameter of said main body portion of said wire to a size corresponding to the inner diameter of said coil spring, defining a reduced uniform diameter portion with a generally annular planar metallic end surface for said wire intermediate its main body portion and its tapered portion, a plurality of convolutions of said coil spring at the proximal end of said coil spring encircling the reduced diameter portion of said wire, and the most proximal convolution abutting said planar metallic end surface, and means securing said proximal end of said coil spring to said wire at said reduced diameter portion of said wire, the junction of said main body portion of said wire and the most proximal convolutions of said coil spring being substantially free of plastic material, the outer diameter of said coil spring being substantially the same as the outer diameter of said main body portion of said wire, providing a smooth transition for the outer surface of the guide wire at the junction of said main body portion of said wire and the most proximal convolutions of said coil spring, thereby facilitating relative movement between the guide wire and the surgical instrument while the guide wire is located within the surgical instrument in use within the body.

14. A guide wire according to claim 13, wherein the length of said reduced diameter portion of said metal wire is in the range of 0.25 to 0.75 inches.

15. A guide wire according to claim 13, wherein said means securing said proximal end of said coil spring to said metal wire comprises solder.

16. A guide wire according to claim 13, wherein said means securing said proximal end of said coil spring to said metal wire comprises a weld.

17. A guide wire according to claim 13, wherein said distal end of said metal wire is tapered over only a portion of its axial extent.

18. A guide wire according to claim 17, wherein said tapered portion of said wire has a generally rectangular cross section.

19. A guide wire according to claim 13, wherein the distal end of said wire extends within said coil spring to the distal end of said coil spring, and comprising means securing said distal end of said coil to said distal end of said wire.

* * * * *